Figure 1:
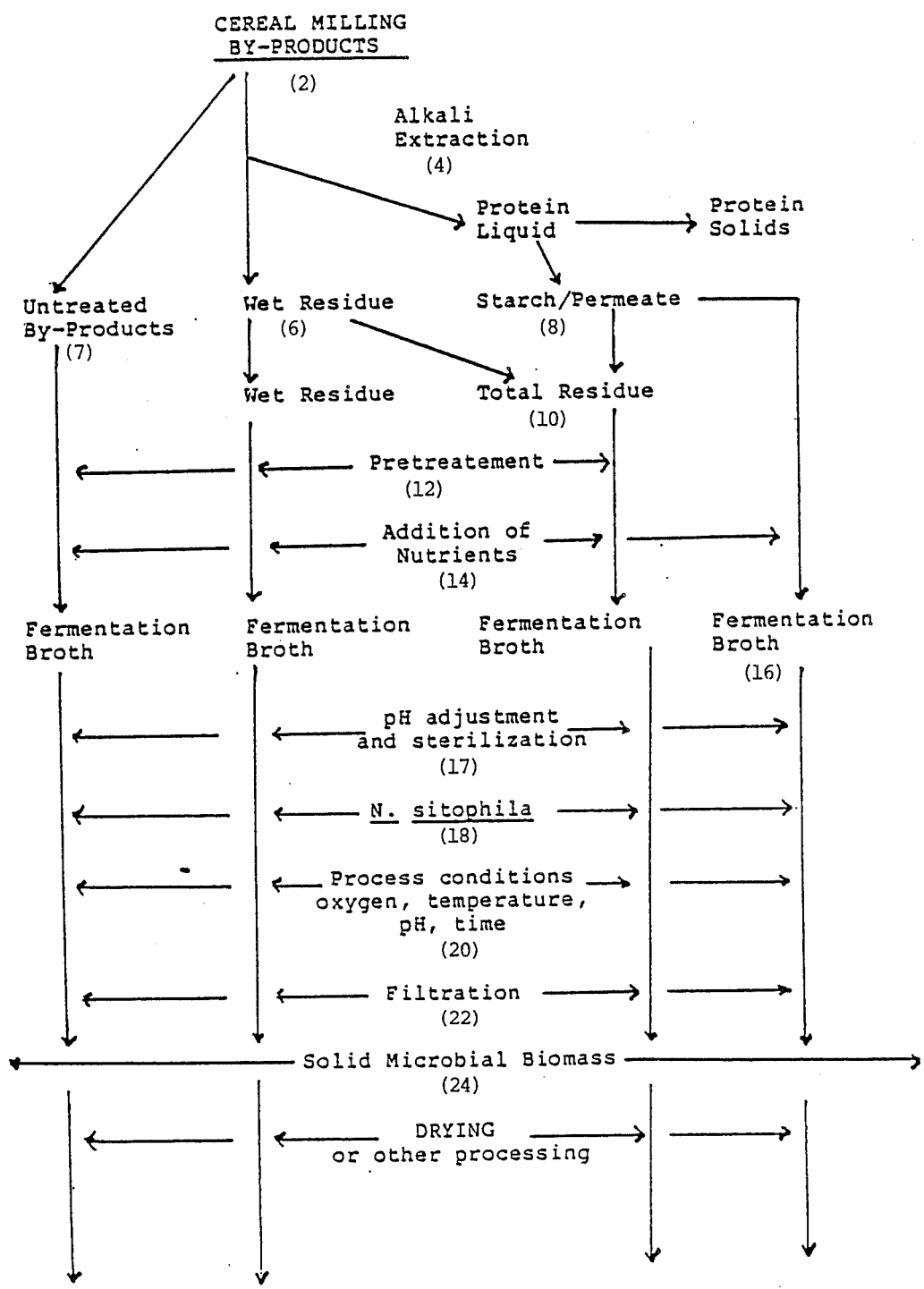

United States Patent [19]

Moo-Young et al.

[11] Patent Number: 4,938,972
[45] Date of Patent: Jul. 3, 1990

[54] PROCESS FOR UPGRADING CEREAL MILLING BY-PRODUCTS INTO PROTEIN-RICH FOOD PRODUCTS

[75] Inventors: Murray Moo-Young, Waterloo; Robert E. Burrell, Kingston; John Michaelides, Mannheim, all of Canada

[73] Assignee: Robin Hood Multifoods Inc., Ontario, Canada

[21] Appl. No.: 217,008

[22] Filed: Jul. 8, 1988

[51] Int. Cl.⁵ .............................................. A23L 1/00
[52] U.S. Cl. ........................................ 426/31; 426/5; 426/7; 426/61; 426/436
[58] Field of Search ...................... 126/7, 31, 61, 436, 126/5

[56] References Cited

U.S. PATENT DOCUMENTS

| | | | |
|---|---|---|---|
| 3,968,035 | 7/1976 | Howe | 427/7 |
| 4,401,680 | 8/1983 | Young | 426/56 |
| 4,482,574 | 11/1984 | Lee | 426/56 |

OTHER PUBLICATIONS

Prescott et al., 1988, 4th Ed., Prescott & Dunn's Industrial Microbiology, p. 515.

Primary Examiner—Donald E. Czaja
Assistant Examiner—Helen Pratt
Attorney, Agent, or Firm—Foley & Lardner

[57] ABSTRACT

The invention provides a process for the microbial bioconversion of cereal milling by-products into proteinaceous material for human consumption. The by-products are aerobically fermented in a culture of the fungus *Neurospora sitophila* in the presence of suitable temperature, pH and nutrient conditions, for a time sufficient to grow microbial biomass protein.

15 Claims, 1 Drawing Sheet

PROCESS FOR UPGRADING CEREAL MILLING BY-PRODUCTS INTO PROTEIN-RICH FOOD PRODUCTS

The present invention relates to microbial bioconversion of cereal milling by-products to form a protein rich product for human or animal consumption.

Cereal (and in particular wheat) milling by-products contain parts of the cereal grain left over after recovery of flour and germ. The outer layers of the seed which include the pericarp (bran) and seed coat comprise the largest components of milling by-products. Cereal milling by-products amount to approximately one-fourth (by weight) of the original raw material. The wheat milling industry is therefore a source of very large quantities of wheat milling by-products. Such cereal milling by-products, by their very nature, are non-digestible by humans and many animals, and furthermore, are generally resistant to microbial degradation even though they usually contain approximately 14% protein and 35-40% carbohydrates (by weight). Although cereal milling by-products have heretofore been utilized as an animal feed ingredient, most of this material is under-utilized and represents a potentially valuable feedstock for fermentation processes in the production of microbial biomass intrinsically useful a generic human food or animal feed product.

It is known to utilize by-products from the petroleum industry and organic solvents for microbial biomass production for animal or human food.

It is also known (Canadian Pat. No. 1,129,709, issued Aug. 17, 1982, Moo-Young) to utilize agricultural cellulosic waste products to form proteinaceous product for animal consumption. This process comprises effecting fermentation of non-food grade cellulosic material by the non-food grade fungus *Chaetomium cellulolyticum* at an optimum growth temperature of 37° C.

It is further known to recover protein from cereal milling by-products by way of alkali extraction followed by acid precipitation or other protein recovery techniques.

The present invention is concerned with the utilization of cereal milling by-products, especially wheat cereal millfeeds, in which the food-grade fungal organism, *Neurospora sitophila*, is mass cultivated in a fermentation bioconversion process to produce a protein rich product. The resulting microbial biomass product has a relatively high content of protein, dietary fibre, ergosterol, natural flavour compounds and B vitamins. The biomass lacks animal fat and cholesterol. As animal feed, this product appears to be competitive with soy meal and fish meal. As a human food, this product appears suitable for special health conscious groups who seek vegetarian, high-fibre and/or low cholesterol diets.

The present invention overcomes the following disadvantages existing in the prior art.

The present invention uses a food-grade organism which does not contravene the U.S., Food & Drug Administration guidelines, the so-called GRAS list (Generally Regarded As Safe). The present invention uses as a raw material, food-grade feedstock which is derived from an acceptable and known agro-food resource as distinct from non-food industrial materials such as petroleum based hydrocarbons and alcohols, or forestry-based wood and paper. The present invention also utilizes technology which is based on solid-substrate fermentation as distinct from gaseous and liquid materials. A solid-substrate is easier to work with. The present invention also uses a multicellular fungal organism as distinct from unicellular organisms such as bacteria or yeasts, which cannot be easily filtered due to their size. The present invention further utilizes a microorganism which has an optimum growth temperature of approximately 26° C. Such a lower temperature reduces the risk of opportunistic infections in humans (body temperature is 37° C.), providing a safer environment for personnel involved in utilizing the invention. Furthermore, in addition to being able to utilize readily digestible carbohydrates such as starches and hydrolyzates, *Neurospora sitophila* possesses cellulolytic enzymes enabling it to utilize the recalcitrant cellulose component present in the majority of cereal milling by-products.

The present invention provides a process for the production of a proteinaceous material comprising: aerobically fermenting, the by-products of cereal milling, in a culture of the fungus *Neurospora sitophila*; at a pH of 5.5-7.5; with agitation; in the presence of a suitable nutrient broth; at a temperature of 20°-40° C.; and for a time sufficient to grow microbial biomass protein.

The organism, *Neurospora sitophila* has been consumed by mankind in Indonesia for hundreds of years, as part of oncom or ontjom an oriental food prepared by the solid state fermentation of peanut presscake and solid waste from tapioca manufacture. The fermentation is carried out at room temperature for 36 to 48 hours. The initial pH of the presscake is approximately 4.5 and it gradually rises as the fermentation progresses. Moderate aeration and humidity of approximately 90% is required during the process. The principal microoganisms involved in the fermentation of peanut presscake belong to the Genus *Neurospora* with several species involved: *N. sitophila*, *N. crassa* and *N. intermedia*. However, since the fermentation is not carried out under controlled monoculture conditions, other microorganisms such as yeasts and bacteria are present. The essential role of *Neurospora* in this process is the enzymatic hydrolysis of protein and starches of the substrate. Such action on the high protein presscake produces easily digestible and more flavourful food due to the formation of shorter protein peptides and amino acids. Consequently, the food-grade safety of this fungus has, to some extent been tested. As a result of experimentation, the present inventors have discovered that *Neurospora sitophila* can be cellulolytic and that it has good growth characteristics on both insoluble lignocellulosic and soluble carbohydrate based media. The inventors have also found that *Neurospora sitophila* demonstrates surprisingly significant speed of growth and diversity of advantages over other microorganisms known in the prior art in relation to the production of microbial biomass.

The present invention is a controlled monoculture fermentation process of cereal milling by-products. In addition to the utilization of starch and easily digestible carbohydrates, the recalcitrant lignocellulosic component of the by-products is chemically and enzymatically broken down by the *Neurospora sitophila*. This is achieved in the invention process by softening and loosening the bonds between lignin and cellulose through an alkali pretreatment followed by enzymatic hydrolysis of cellulose by the various cellulases produced by the fungus during fermentation. The product of such hydrolysis are in turn used for the production of additional fungal biomass, thus substantially increasing the protein content of the final product of the fermentation.

The cereal milling by-products are utilized in the form of a solid-liquid slurry, as is or after deproteination with caustic leaching. The fermentation medium is seeded with an inoculum of the fungus N. sitophila prepared according to well-established standard protocols. Preferably the cereal is wheat.

The aerobic fermentation should occur in the environment of means for creating low shear aeration-agitation conditions. The aerobic fermentation broth should contain dissolved oxygen equal to approximately 50% air saturation. Levels below 30% will result in significant reduction in yields.

Neurospora sitophila is grown until the fermentation broth consists of over 50% (on a dry weight basis) of the fungal biomass, or the fungus reaches a "stationary growth phase" according to the principles of fermentation technology. A suitable nutrient broth should be used, which preferably has a nitrogen content of 50-75% (by weight) of the "basic nutrient composition" preferably in the form of ammonium sulphate and urea. The fungal biomass may be separated from the fermentation broth by filtration or other separation techniques known to those skilled in the art. It may also be dried for storage and/or transportation purposes.

Table 1 below shows the nutritional quality of the resulting fungal protein product based on its composition of "essential amino acids", compared with fodder yeast (Candida utilis), soymeal and the guidelines on human food of the United Nation's Food and Agriculture Organization (FAO). It should be noted that the generic microbial protein product of the present invention compares well to the other amino acid distribution profiles (the important guideline for nutritional protein quality). In particular, the sulfur containing amino acids (cystine and methionine) are present in comparable or higher amounts than other microbial proteins such as fodder yeast.

TABLE 1

Essential amino acid compositions (as % by weight total protein) for various protein products and the microbial biomass of the present invention

| Amino Acid | FAO Reference | Soybean Meal | Fodder Yeast | N. sitophila | | |
|---|---|---|---|---|---|---|
| | | | | S/P | W/R | T/R |
| Isoleucine | 4.2 | 4.3 | 5.3 | 5.59 | 4.96 | 5.07 |
| Leucine | 4.8 | 7.6 | 7.0 | 9.26 | 7.96 | 8.17 |
| Lysine | 4.2 | 5.7 | 6.7 | 5.09 | 5.32 | 5.30 |
| Phenylalanine | 2.8 | 4.8 | 4.3 | 4.02 | 4.15 | 4.14 |
| Tyrosine | 2.8 | 3.6 | 3.3 | 1.93 | 2.11 | 2.09 |
| Cystine | 2.0 | 1.98 | 0.7 | 0.44 | 0.75 | 0.71 |
| Methionine | 2.2 | 1.14 | 1.2 | 1.06 | 1.81 | 1.70 |
| Threonine | 2.8 | 3.8 | 5.5 | 3.26 | 3.81 | 3.74 |
| Tryptophan | 1.4 | 1.6 | 1.2 | 2.46 | 2.94 | 2.88 |
| Valine | 4.2 | 4.4 | 6.3 | 7.43 | 6.94 | 7.03 |

S/P - produced from starch permeate.
W/R - produced from wet residue.
T/R - produced from total residue.

Table 2 below provides proximate values of the key food parameters for the generic product (microbial biomass per se). Compared to animal meat such as beef, the generic product has desirably higher proportions of protein and dietary fibre. In addition, it contains no cholesterol thus making it a healthier food, in theory, than traditional livestock meat products.

TABLE 2

Proximate composition (% dry weight) of microbial biomass produced from cereal milling by-products utilizing N. sitophila

| Component | Amount |
|---|---|
| Crude Protein | 30-60%* |
| Total Dietary Fibre | 40%* |
| Fat | 5% |
| Cholesterol | 0% |

*The amount of protein and total dietary fibre varies with the substrate used.

The good quality of the microiial biomass product from this microorganism has been confirmed in feeding trials using rats. In these studies, final products from starch permeate and wet residue fermentations were evaluated for palatability and protein efficiency ratio against casein standard diets with encouraging results.

In the process of the present invention, cereal milling by-products may be utilized in their existing form, or in the form of either a "wet residue", the combined "starch and permeate" or "total residue". Cereal milling by-products may be subjected to aqueous alkaline extraction in order to extract protein. The separation of the proteinaceous extract from the solid residue results in a "wet residue". Applying further physical separation techniques to the proteinaceous extract yields "starch" and a "permeate". The wet residue, the combined starch and permeate or a combination of the two: "total residue", represent three streams of the extraction process which may be subjected to fermentation with N. sitophila for the production of microbial biomass protein. The raw by-products of cereal milling prior to extraction (alone or combined with the extracts and residues) may also be subjected to fermentation by the same fungus.

Feedstocks or streams which contain ligno-cellulosic materials require pretreatment prior to utilization by the microorganism. These streams are the total residue, wet residue or any cereal milling by-products which are not deproteinated.

Pre-treatment of the wet residue with heat in the presence of alkali demonstrated an improved rate of bioconversion. In a lignocellulosic material such as wheat milling by-products, the ratio of cellulose to lignin is very important since the lignin content directly affects the availability of the cellulose. In typical structural and protective elements in plants, lignin impregnates the cellulose of the cell-wall, where it acts as a protective cement. In cereal milling by-product raw material, the ratio of cellulose to lignin was found to be 1:1 which is extremely high and indicates that any bioconversion process would be slowed. In the insoluble lignocellulosic residue (wet residue) remaining after deproteination, the cellulose to lignin ratio was found to be 2:1. Biodegradability of most lignocellulosic materials will increase if the lignin is either partially or fully removed. This may be achieved by the use of a caustic solution in conjunction with high temperatures Such pretreatment solublizes the lignin and swells the cellulose which allows for greater penetration of the cellulaze enzymes (present in the fungus) and henc greater degradation of the cellulose.

In the process of the present invention pretreatment was carried out in a solution of 0.25-1% NaOH W/V and slurry concentrations of 7-10% w/v solids. The pretreatment temperature can range from 121° C. to 165° C. under the appropriate pressure and retention times of 4 to 30 minutes. The mixture is then diluted to an appropriate concentration for the required fermentation and the pH adjusted prior to sterilization.

The drawing attached hereto as FIG. 1 is a flow chart which illustrates four embodiments of the present invention. Referring to the flow chart, cereal milling by-products 2 may be deproteinated by alkali extraction 4 which may be followed by acid precipitation and filtration (or other means of isolation) to produce wet residue 6 and starch and permeate (hereinafter "starch permeate") 8. The starch permeate may be admixed with the wet residue to form a total residue 10. Alternatively, the process of the present invention may be applied to untreated cereal milling by-products as at 7. Four embodiments of the present process are reflected in Flow Chart 1 as the process streams, namely, wet residue, starch permeate, total residue and untreated by-products. Pretreatment 12 of the untreated by-products 7, the wet residue 6 or the total residue 10 as aforesaid will partially delignify the solid particulates therein. Table 3 shows the utilization of cellulose in the wet residue as related to the amount of sodium hydroxide in the pretreatment.

TABLE 3

Utilization of Cellulose in Wet Residue by *N. sitophila* Under Pretreatment Conditions Containing Various Amounts of NaOH

| Level of NaOH % w/v | Cellulose Concentration in Fermentation Broth g/L | | % Cellulose Utilization |
|---|---|---|---|
| | 0 Time | 24 Hours | |
| 0 | 1.60 | 1.45 | 9.4 |
| 0.10 | 1.58 | 1.47 | 7.0 |
| 0.25 | 1.49 | 0.94 | 37.0 |
| 0.50 | 1.53 | 0.48 | 68.6 |
| *1.00 | 2.25 | 0.25 | 88.9 |

Shake flask experiments.
*Pilot scale 1,000 L fermentor.

Following the pretreatment 12 an appropriate nutrient broth (basic nutrient composition) is added. The pretreated solids are supplemented with chemicals in the form of a nutrient broth 14 according to known standard procedures such that the available carbon, nitrogen, phosphorus and potassium are in appropriate ratios to form a fermentation medium or broth 16. The solid-liquid slurry of cereal milling by-products used as a fermentation medium is diluted with water to a concentration in the range of 0.5% to 3.0% (w/v) solids and supplemented with the appropriate nutrients in a mixing tank. The nutrients may have the following composition per 1,000 litres of fermentation medium: Ammonium sulphate $(NH_4)_2SO_4$:472 grams, Urea $CO(NH_2)_2$:856 grams, potassium phosphate monobasic $KH_2PO_4$: 2,000 grams, magnesium sulfate seven hydrate $MgSO_4.7H_2O$:200 grams, Calcium chloride $CaCl_2$: 200 grams, Zinc sulfate seven hydrate $ZnSO_4.7H_2O$:4.4 grams, ferric chloride six hydrate $FeCl_3.6H_2O$:3.2 grams, Boric acid $BH_3O_3$:0.114 grams, Ammonium molybdate four hydrate $(NH_4)_6Mo_7O_{24}.4H_2O$:0.489 grams, Cupric sulfate five hydrate $CuSO_4.5H_2O$:0.789 grams, manganese chloride four hydrate:0.144 grams. These nutrients comprise the "basic nutrient composition" and may be used in full or in part, individual compounds may be varied or omitted, or additional ones may be used depending on the nature of the fermentation medium. The scope of such variation will be apparent to those skilled in the art.

Nitrogen in the nutrient broth may be supplied as $(NH_4)_2SO_4$ and urea. In the case of wet residue, optimal nitrogen and substrate utilization occurs when the nitrogen content of the fermentation broth is 50% to 75% (by weight) of the basic nutrient composition. Experimentation further indicated, that *Neurospora sitophila* grown on starch permeate requires at least 75% (by weight) nitrogen of the same composition for maximum growth rate and protein production.

In the case of both wet residue and starch permeate, it was determined there is no requirement for added phosphorus. Growth at the zero addition level was not significantly different from growth in the full phosphorus treatment. Consequently, naturally occurring phosphorus in the substrate is adequate.

Similarly, tests showed that trace elements present in the pretreated wet residue and starch permeate are sufficient to support the growth of *Neurospora sitophila* without supplementation. This is a further economic advantage present in the use of the present process.

The mixture 16, after the addition of nutrients 14, is then adjusted to an appropriate pH and passed through batch mode sterilization (121° C. and necessary time) or a continuous sterilizer at approximately 165° C. with retention time of 0.25–3.0 minutes. It is then diverted into the fermentor vessel where the temperature of the medium 17 is adjusted to 20°–40° C. and preferably 26° C., and seeded with a precultivated inoculum 18 of *N. sitophila*. The level of the inoculum may vary from 3% to 10% of the fermentor working volume. Process conditions 20 include oxygen, agitation, temperature, pH and time. The mixture is subjected to special low-shear aeration-agitation conditions at an air supply of 0.5 to 1.0 VVM (Volume of air per Volume of medium per Minute) at a temperature 20°–40° C. and preferably 26° C. and a pH range of 5.5 to 7.5, depending on the type of by-product or stream to be fermented. The said fermentor vessel is equipped with sensors and controls for pH (acid or alkali addition), antifoam, oxygen consumption and carbon dioxide evolution. It is specifically designed to supply aeration and agitation which is conducive to the requirements of *N. sitophila* which was found to be shear sensitive.

An air lift fermentor device is ideally suited. It has low local shear conditions combined with excellent mixing capabilities and has the added benefit of reduced power requirements for operation. Further, with no need for impellers, the risk of contamination through a physical failure of the drive shaft seals is greatly reduced insuring continuity of operation.

The biomass of the fungus should be grown until the final product consists of over 50% of the fungus on a dry weight basis, or the fungus reaches a stationary growth phase. At this point harvesting will take place (batch fermentation) or continuous fermentation will be initiated.

Once the fermentation is completed and a sufficient biomass of fungus has been grown, it may be isolated from the fermentation broth by filtration (or other suitable separation technique) as at 22. This produces a solid microbial biomass product 24 which thereafter may be dried by appropriate means known to those skilled in the art.

The end fermentation product may be further processed as follows: The broth from the fermentor vessel can be removed by level control or a pumping device and concentrated by removal of the liquid by filtration, centrifugation or other means of separation. The liquid waste is discarded and the concentrated slurry of microbial biomass can be further treated by drying using various means; freeze dried preserved frozen or further wet processed, to fit its end use.

Various experiments were carried out to optimize the systems and operating variables of the fermentation process. Table 4 below shows typical results of the process based on typical values of the following system variables: slurry concentration of the fermentation medium =2% weight per volume basis; temperature =26° C.; pH =6.7; dissolved oxygen in the medium=50% of air saturation. The table reveals that for the two types of by-product residue (namely wet residue and total residue), microbial biomass in the range of 64 to 72% (dry weight basis) was formed by the process invention, from the original material which contained virtually no protein. Table 4 also reveals that comparable degrees of bioconversion in terms of microbial biomass composition of the product are obtained in relatively shorter fermentation periods when the process is conducted in relatively low-shear bioreactor devices of the air-lift type, than in the relatively high-shear bioreactor devices of the more conventional mechanically-stirred type.

TABLE 4

| | Microbial Biomass Production in Different Bioreactor Types | | | |
|---|---|---|---|---|
| | Mechanically Stirred Bioreactor | | Air-Lift Bioreactor | |
| Residue Type | % Biomass (dry weight basis) | Time (hours) | % Biomass | Time (hours) |
| Wet residue | 64 | 40 | 72 | 16 |
| Total residue | 72 | 28 | — | — |

The results of Table 5 below, further illustrate the beneficial effect of the low-shear conditions of the fermentation bioreactor in microbial biomass formation. In this case, the starch permeate liquid mixture was used to cultivate the fungus.

TABLE 5

| Cultivation Times for Equal Conversion Levels of Starch Permeate Substrate to Microbial Biomass in Two Bioreactor Types | |
|---|---|
| TYPE | TIME |
| Mechanically stirred Bioreactor: | 31 hours |
| Air-Lift Bioreactor: | 18 hours |

The process of the present invention may be performed as a batch or continuous run process. In addition, the protein quality may be improved by genetic techniques dependent upon the presence of a sexual stage which *Neurospora sitophila* has as an ascomycete. The use of the optimal form of the fungus may further improve protein quality.

Illustrative Examples

Example 1: Batch Fermentation of Total Residue:

Following the general protocol described earlier, a fermentation was carried out using total residue as the substrate. The wet residue component of the total residue was pretreated at 10% (w/v) slurry at 121oC for 30 minutes with 1% (w/v) NaOH. The starch permeate and pretreated wet residue were then combined and added to a 15L fermentor (MBR Switzerland), so that the final concentration of solids was 2% w/v. Appropriate nutrients (described earlier) were then added in full and the pH of the mixture adjusted to 6.0. The medium was then sterilized in situ, at 121° C. for 15 minutes, cooled to 26° C. and inoculated with precultivated *N. sitophila* at a level of 10% (v/v) of the fermentor working volume. The fermentor was equipped with pH control (addition of $H_2SO_4$ or NaOH accordingly) and antifoam control. The temperature was maintained at 26° C. and the dissolved oxygen at more than 50% of saturation by sparging air and agitation. Carbon dioxide, dissolved oxygen, pH and temperature were monitored throughout the fermentation. Samples of fermentation broth were taken at regular intervals and subjected to the following analysis: total solids, crude protein, reducing sugars cellulose and total carbohydrates. At the end of fermentation (36 hours) the broth contained 2.24 g/L protein; an increase from 0.50 g/L. The harvested broth was then concentrated by filtration and dried at temperatures of about 60°–70° C. The dried product contained 34% (dry weight) crude protein.

Example 2: Batch Fermentation of Wet Residue Pilot Plant Scale:

Fermentation was carried out in a 1,000 L pilot plant using wet residue as a substrate. The wet residue was pretreated as described in the previous example. Water was then added to the fermentor so that the medium reached a solids concentration of 1.6% w/v. A full compliment of nutrients was added and the pH of the broth was adjusted to 6.0. Sterilization was carried out in situ as described in the previous example, and following cooling to 26° C., the medium was inoculated with precultivated *N. sitophila* using a 3% (v/v) level of inoculum. Parameters were monitored and controls were carried out as in the previous example. No mechanical agitation was carried out, but air was sparged from an annular ring at the base of the fermentor vessel at the rate of 0.8 VVM.

The fermentation was completed in 46 hours and at termination, the protein level in the broth was 2.6 g/L. The broth was concentrated to 15 to 20% (w/v) solids using a centrifuge and dried to 4–10% moisture level at 60°–70° C. The final product contained 32% w/v crude protein.

Example 3: Continuous Fermentation in Pilot Scale Plant Using Starch Permeate

The total available substrate for fermentation was (starch permeate mixture) 53.315kg solids in 5270 L of water (1.01% w/v). To further extend the fermentation time, the fermentor was operated below capacity at 790 L which enabled 7 volumes to pass through it and thus achieve steady state conditions.

Operating conditions for the fermentor were as follows: air supply 0.8 VVM, pH 6.7, temperature 26° C. and dilution rate 0.235 $h^{-1}$. The continuous sterilizer was operated at 165° C. with a 2.08 minute retention time. The temperature of the feedstock at the fermentor inlet head was 35° C. Additional cooling was required from the fermentor cooling coils during the entire fermentation.

Harvest of the microbial biomass protein was accomplished by feeding a continuous centrifuge (10,000 rpm) from a Moyno (trade mark) pump at the desired rate. Immediately after harvesting, the microbial biomass protein product was frozen. The frozen material was later oven dried at 60° C. and then ground.

Samples (750 ml) of the fermentor broth were taken periodically and analyzed for total dry weight, crude protein, soluble nitrogen and soluble carbohydrates.

After an initial batch time period of 15 h, continuous operation was started and maintained for 25.5. h. The average protein content was 48% (dry weight) and the protein concentration was in excess of 1.6 g/L. The level of nitrogen in the effluent indicated that the amount supplied was in excess of the amount required. After the third volume had passed through the fermentor, there was little fluctuation in the nitrogen level of the effluent. This indicated that steady state conditions existed in the fermentor. This was verified by both the dissolved oxygen in the fermentor broth and the $CO_2$ in the effluent gas which did not vary after the third volume.

The harvested material, with a moisture content of 85% was dried at 60° C. to avoid damage to the protein. The final product yield was 16.763 kg (16.713 kg +0.05 kg sampled) of microbial biomass protein from 53.315 kg substrate or 0.31.

Example 4: Continuous Fermentation Pilot Plant Scale Using Wet Residue

This fermentation utilized wet residue in the amount of 604.4 kg containing 29.8% solids (180.1 kg). This material was adequate to run 9 volumes through the fermentor on a continuous basis at 2% solids (w/v). This mass of material was pretreated in a caustic solution to solubilize the lignin and increase cellulose availability. To pretreat the substrate it was diluted to 7.5% solids (w/v) with 1% NaOH solution (1795.6 L) and run through the continuous sterilizer at 165° C. with a retention time of 4.5 minutes. The pretreated wet residue was stored in polyethylene tanks at pH 12 until it was required for fermentation. The pretreated wet residue was transferred into a suitable vessel and diluted with water to contain 2% solids w/v. A full compliment of nutrients was added with the exception of nitrogen and phosphorus, which were adjusted to 75% and 10% of their original values respectively. The pH was adjusted to 6.0 and the slurry passed through the continuous sterilizer at 165° C. with retention time of 2.05 minutes. Following an initial 24 hour batch operation, subsequent volumes of medium were prepared as above and the fermentor was fed in a continuous mode at a 1,000 L operating level, for a total of nine volumes.

Operating conditions for the fermentor were as follows: air supply 0.8 VVM, temperature 26° C. and dilution rate 120 L/h. The continuous sterilizer operated at 165° C. with a 2.05 minute retention time. The feedstock temperature was 40° C. at the fermentor head. Dissolved oxygen and CO2 in the effluent gas were monitored throughout the experiment.

Harvest of the microbial biomass protein was accomplished using a continuous centrifuge (10,000 rpm). Immediately after harvesting, the product was frozen. The frozen material was either oven dried at 60° C. and ground or it was thawed and spray dried.

Samples (750 mL) of the fermentor broth were taken periodically and analyzed for total dry weight, crude protein, soluble nitrogen and total carbohydrates.

Continuous mode was initiated after 24 h of batch growth during which time $\mu$max was calculated to be $0.23 lh^{-1}$. The percent protein peaked at 40% (2.5 g/L) dry weight eight hours after continuous operation began and dwindled to 32% (2 g/L) by the end of the run. The level of residual cellulose was at a minimum after 24 h and although it remained low for the duration of the experiment, there was an upward trend that matched the decline in protein.

Measurements of total carbohydrates and cellulose indicated that the only residual carbohydrate in the solid matter was cellulose and that an average, 86-90% of it was utilized during the continuous phase.

The total mass of microbial biomass protein product generated was estimated at 63 kg (dry). This was derived from 180 kg (dry) of substrate for a product yield of 0.35, containing approximately 40% (w/w) crude protein.

Variations of the process described herein and advantages of the present invention, beyond those mentioned herein, will be apparent to those skilled in the art.

The embodiments of the invention in which an exclusive property or privilege is claimed are defined as follows:

1. A process for the production of a proteinaceous material suitable for human consumption, from the by-products of cereal milling including cellulose, comprising:
   aerobicially fermenting, said by-products in a culture of the fungus *Neurospora sitophila*;
   at a pH of 5.5-7.5;
   with agitation;
   in the presence of a suitable nutrient broth;
   at a temperature of 20°-40° C.; and
   for a time sufficient to increase the microbial biomass protein to yield a proximate composition including 30-60% crude protein on a dry basis.

2. The process of claim 1 wherein said aerobic fermentation occurs in the presence of means for creating low-shear aeration-agitation conditions.

3. The process of claim 2 wherein said means for creating low-shear aeration-agitation conditions is a device of the air-lift type.

4. The process of claim 3 wherein the by-products of cereal milling may be utilized untreated or as treated after protein extraction in the form of either a wet residue, a starch permeate, a total residue or a combination thereof.

5. The process of claim 4 wherein the untreated by-products, wet residue and total residue contain solids which are pretreated prior to aerobic fermentation to soften and partially delignify said solids.

6. The process of claim 5 wherein the solids are pretreated with a caustic solution admixed with a solution of non-carbon nutrient supplement.

7. The process of claim 6 wherein said caustic solution is a 0.25%-1% w/v solution of NaOH mixed with the solids to form a 7%-10% w/v slurry which is heated under pressure for 4-30 minutes at 165° C.-121° C.

8. The process of claim 6 wherein said caustic solution is a 1% w/v solution of NaOH mixed with the solids to form a 10% w/v slurry which is heated under pressure for up to 30 minutes at 121° C.

9. The process of claim 7 wherein said microbial biomass protein is grown until the finished product consists of over 50% of the fungus on a dry weight basis, or the funqus reaches a stationary growth phase.

10. The process of claim 9 wherein said aerobic fermentation occurs in the presence of dissolved oxygen equal to approximately 50% air saturation.

11. The process of claim 9 wherein said suitable nutrient broth is the basic nutrient composition having a nitrogen content of 50%-75% (by weight), of its original value.

12. The process of claim 11 wherein said microbial biomass protein grows in a fermentation broth and is separated therefrom by filtration.

13. The process of claim 12 wherein said aerobic fermentation occurs at a pH of 6, or 6.7 depending on the substrate.

14. The process of claim 13 wherein said aerobic fermentation occurs at a temperature of 26° C.

15. The process of claim 1, 2 or 3 wherein said cereal is wheat.

* * * * *